United States Patent [19]

Suzuki et al.

[11] Patent Number: 5,115,130
[45] Date of Patent: May 19, 1992

[54] SURFACE MEASURING METHOD AND APPARATUS

[75] Inventors: Keizo Suzuki, Kodaira; Ken Ninomiya, Higashimatsuyama; Takashi Yunogami, Kokubunji, all of Japan

[73] Assignee: Hitachi, Ltd., Tokyo, Japan

[21] Appl. No.: 536,152

[22] Filed: Jun. 7, 1990

[30] Foreign Application Priority Data

Jun. 9, 1989 [JP] Japan .................................. 1-145328

[51] Int. Cl.⁵ ................................................ H05H 3/00
[52] U.S. Cl. .................................. 250/251; 250/505.1
[58] Field of Search .............................. 250/251, 505.1

[56] References Cited

U.S. PATENT DOCUMENTS

| | | | |
|---|---|---|---|
| 4,629,899 | 12/1986 | Plies | 250/251 |
| 4,775,789 | 10/1988 | Albridge et al. | 250/251 |
| 4,886,964 | 12/1989 | Pritchard et al. | 250/251 |
| 4,992,656 | 2/1991 | Clauser | 250/251 |

OTHER PUBLICATIONS

"Atomic beam spectrometer for Surface Investigation"-Scherb et al., *Rev Sci. Inst.*, vol. 47, No. 12, Dec. 1976, pp. 1511–1515, 250–251.
"Structure and Dynamics of Surfaces I", W. Schommers et al, pp. 56–65, 245–277, 1986.

*Primary Examiner*—Bruce C. Anderson
*Attorney, Agent, or Firm*—Fay, Sharpe, Beall, Fagan, Minnich & McKee

[57] ABSTRACT

A surface measuring method and apparatus utilizes a low energy neutral particle (neutral atom, neutral molecule) controlled to be equal to or lower than 1 eV, which is caused to collide against the surface of a specimen. A neutral particle reflected at the specimen surface is detected, and its energy is measured to nondestructively measure the chemical bonding state of the specimen surface.

30 Claims, 3 Drawing Sheets

SURFACE MEASURING METHOD AND APPARATUS

BACKGROUND OF THE INVENTION

The present invention relates to surface measurement technology, and more particularly to a surface measuring method and apparatus using a low energy neutral particle (neutral atom, neutral molecule) beam.

With recent development of devices having a solid body surface, ultra thin film (super lattice film) and the like, a desire to measure the chemical bonding state of surfaces is increasing more and more. Particularly, a desire to measure the chemical bonding state of small surface areas (characteristic length representative of the dimension of an area to be measured, is shorter than or equal to 1 μm, or more severely 1 nm) is increasing nowadays.

As conventional methods for measuring the chemical bonding state, there are known a method using an electron beam such as Electron Energy Loss Spectroscopy (EELS), a method using an ion beam such as Ion Scattering Spectroscopy (ISS), and a method using an X-ray such as X-ray Photoemission Spectroscopy (XPS). These methods are described in "Structure and Dynamics of Surfaces I", edited by W. Schommers and P. von Blanckenhagen, Springer-Verlag, Tokyo (1986), respectively at pp. 245 to 276 for EELS, at pp. 56 to 61 for ISS, and at p. 63 for XPS.

With the EELS method, an electron beam of several tens eV is applied to a specimen surface, and the energy of reflected electrons is analyzed to determine the chemical bonding state of atoms and molecules on the surface. With the ISS method, an ion beam of several keV is applied to a specimen surface, and the energy of reflected ions is analyzed to measure the surface chemical state. With the XPS method, an X-ray of several hundred eV to several keV is applied to a specimen surface, and the energy of photoelectrons emitted from the surface is analyzed to determine the surface chemical state. These methods, although they provide the surface chemical state, are associated with the following problem. Namely, a specimen surface is damaged (chemical bonding state is changed) during the measurement because of excessive energy of a particle beam (electron beam, ion beam) or an X-ray incident to the surface. This problem essentially arises because the energy of such a particle beam is larger than the intensity of the general chemical bonding state which is 1 to 10 eV.

In order to realize non-destructive surface measurement, the energy of an incident particle beam should be maintained lower than or equal to 1 eV. It is practically difficult, however, to obtain such a low energy electron or ion beam having charged particles. The reason for this is a difficulty in controlling the energy and locus of a particle beam due to distributed space charges of a flux of flying particles having electric charges.

On the other hand, in the case of an electromagnetic wave (light wave in broad sense) such as an X-ray, it is easy to obtain a low energy beam smaller than or equal to 1 eV. However, this is also associated with the following problem. Specifically, the energy E and wavelength λ of light are related to each other by:

$$a = ch/E \qquad (1)$$

wherein c represents the velocity of light, and h represents Planck's constant, so that the smaller the energy E becomes, the longer the wavelength λ becomes. The relationship between the energy E and wavelength λ of light is shown by a line labeled as "LIGHT" in FIG. 2. As seen from FIG. 2, a light wave having an energy E equal to or smaller than 1 eV has a wavelength equal to or longer than 1 μm (i.e., in the infrared region). A light wave having a wavelength equal to or longer than 1 μm cannot be converged smaller than about 1 μm or less because of diffraction and interference. In other words, the method using a light wave (electromagnetic wave) cannot satisfy at the same time both the non-destructive nature of E ≦ 1 eV and the capability of measuring a small area for λ ≦ 1 μm.

A particle beam (electron, ion, atom, molecule, and the like) other than a light wave can also be considered as a wave from the standpoint of quantum mechanics, so that the kinetic energy E and de Broglie wavelength of a particle beam are related to each other by:

$$\lambda = h/\sqrt{2mE} \qquad (2)$$

where m is the mass of a particle. As understood from the equation (2), even with the same energy E, the wavelength becomes longer as the mass m becomes smaller. The relationship represented by the equation (2) for an electron beam is shown by a solid line indicated "ELECTRON" in FIG. 2. In this case, an electron beam having an energy E equal to or larger than about $10^{-5}$ eV has a wavelength equal to or shorter than 1 μm, thereby allowing non-destructive small area measurement. An electron beam having a wavelength equal to or shorter than 1 nm, however, requires the energy E which is equal to or larger than 1 eV, resulting in a possibility of surface damage of an ultra-small area equal to or shorter than 1 nm.

As described above, surface measurement using a light wave or charged particle beam may cause surface damage, and it is very difficult to non-destructively measure the chemical bonding state of a small area.

SUMMARY OF THE INVENTION

It is an object of the present invention to provide a method and apparatus for non-destructively measuring a surface, particularly a chemical bonding state, of a small area.

The above object is achieved by using a neutral particle beam as a probe beam.

The relationship given by the equation (2) for a He atom beam is shown by a solid line indicated by "He" in FIG. 2. In this case, a He atom beam having an energy equal to or larger than about $10^{-3}$ eV has a wavelength equal to or shorter than 1 nm, thereby allowing non-destructive measurement of an ultra-small area. In addition, a He atom is a neutral particle so that the particle beam is not disturbed by space charges, facilitating fine area measurement.

Although only He atom beam is shown in FIG. 2, other atoms and molecules have similar relationships, thereby allowing to non-destructively measure the chemical bonding state of a small (ultra-small) area.

Use of a neutral particle beam of atoms or molecules accordingly allows to non-destructively measure a surface, and measure the surface of a small area if the neutral particle beam is converged smaller to the extent as necessary.

PREFERRED EMBODIMENTS OF THE INVENTION

Figure 1:
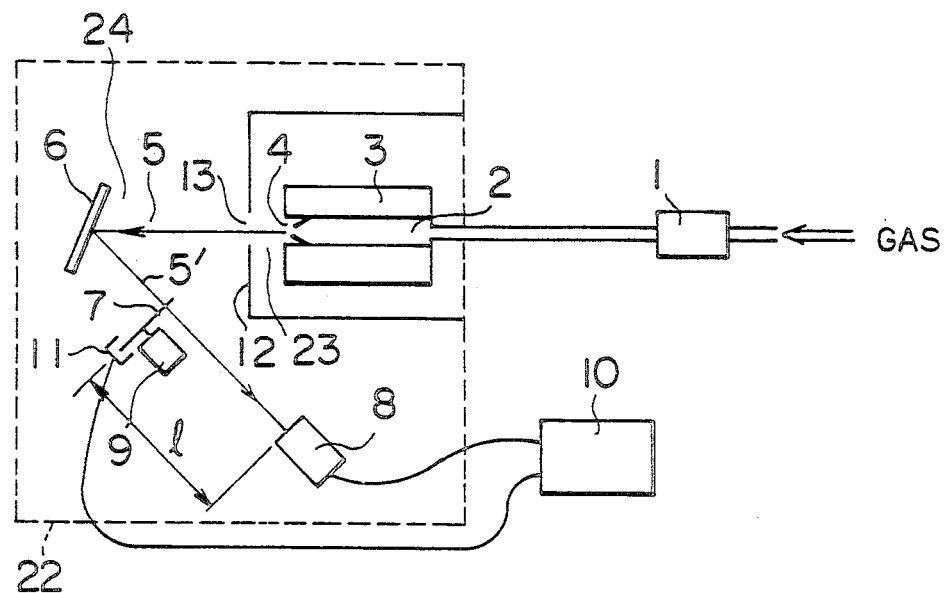
FIG. 1 is a schematic diagram showing an embodiment of this invention.

An embodiment of this invention will be described with reference to FIG. 1. Gas is introduced into a vessel 2 by gas introducing means 1. After the gas is cooled by cooling means 3, it is blown out from a blowout port 4 into a vacuum exhaust chamber 22 which houses therein the entirety of a measuring system. As a result, a neutral particle (atom molecule) beam 5 is generated. The neutral particle beam 5 is reflected or scattered at the surface of a specimen 6. At this time, there is an energy transfer between the specimen surface and neutral particle beam 5. The magnitude or transferred energy depends upon the type of atom/molecule forming the surface and the chemical bonding state thereof. Accordingly, by analyzing the energy of a reflected or scattered neutral particle beam 5′, the chemical state of the specimen surface can be determined. Also by analyzing the transferred kinetic momentum, the state of the specimen surface can be measured.

FIG. 1 illustrates a flying time method which analyzes the energy of a reflected or scattered neutral particle beam 5′. Specifically, a reflected or scattered neutral particle beam 5′ is chopped (transformed into a pulsating flow of neutral particles) by a chopper 7, caused to fly over a predetermined distance l, and detected with a detector 8. The chopper 7 is driven (usually, rotated) by a chopper driving motor 9. The chopper 7 is made of a disk having an opening (slit) so that a pulsating beam is generated as a neutral particle beam which has intermittently passed through the opening. The flying speed of a neutral particle can be obtained by measuring the flying time of the particle by the distance l by means of a flying time measuring system 10. With a known mass of a neutral particle, the energy of the particle can be obtained. ASN opening/closing sensor 11 is used for obtaining the flying time, by measuring the time when a neutral particle passes the chopper 7.

A particle beam generating chamber 23 for generating the neutral particle beam 5 and a specimen chamber 24 for loading the specimen 6 may be separated by a partition wall 12, thereby exhausting (differential pumping) air within the chambers by means of difference exhausting means (not shown). In such a case, the neutral particle beam 5 is guided into the specimen chamber 24 via a pin-hole aperture 13 formed in the partition wall 12. FIG. 1 illustrates one step differential pumping, although the number of steps may by multiple. Similarly, the detector 8 may be housed within a detector chamber (not shown), separate from the specimen chamber 24, with a similar partition wall (not shown) being interposed therebetween, to thereby conduct differential pumping.

He gas is suitable for generating the neutral particle beam 5 because this gas has low chemical action and can maintain a gaseous phase even if it is cooled to a low temperature. Other rare gases such as Rn, Ne, Ar, Kr, Xe or molecules such as $CO_2$, $N_2$, $H_2$, $O_2$ may also be use if desired.

When the gas is blown out from the gas vessel 2 into the vacuum via the blowout port 4, it undergoes adiabatic expansion and its temperature is reduced. Accordingly, a neutral particle beam 5 is generated having a narrow energy distribution width of each neutral particle.

As to the motion of a particle, there is a translation motion having a shift in the center of gravity of a particle, a rotational motion with a rotation of a particle around the center of gravity, and a vibrational motion with a vibration of a particle relative to the center of gravity. The kinetic energy of a particle is represented by a value proportional to the product of Planck's constant and its absolute temperature.

The absolute temperatures representative of the energies corresponding to the half-width values of respective kinetic energies are called translational temperature, rotational temperature, and vibrational temperature.

The translational motion energy becomes largest for a blown-out particle.

The translational temperature Tt of a particle subjected to adiabatic expansion lowers first. Then, in the case of a molecule beam, the rotational temperature Tr and vibrational temperature Tv lower respectively. The higher the gas pressure Pn within the vessel 2, the more extensively the temperature lowers. As to the gas pressure within the vessel 2, the range from $10^{-1}$ to $10^4$ Torr is practically available. In this Pn range from $10^{-1}$ to $10^4$ Torr, the temperatures Tt and Tr generally lower, but the temperature Tv does not. In the Pn range from 10 to $10^4$ Torr, all the temperatures lower. If the gas pressure Pn is too high, the gas flow blown out from the blowout port 4 becomes too large, so that it becomes necessary to use the air-exhausting system of a large scale for exhausting air within the particle beam generating chamber 23 and specimen chamber 24, which is not suitable for a practical use. In order to avoid this, there is a method whereby the blowout port is opened and closed in a pulsating manner (intermittently) to thereby obtain a pulsating neutral particle beam. With such an arrangement, the average gas flow becomes small, and a neutral particle beam of a good quality having low Tt, Tr and Tv, i.e., having a narrow energy distribution width, under a high Pn condition is obtained.

Particles constituting a neutral particle beam are required to fly within the specimen chamber 24 substantially without colliding against the introduced gas which was used for blowing out particles and against the remaining gas not exhausted. For this purpose, it is desirable to set the gas pressure Pn within the specimen chamber 24 equal to or lower than about $1 \times 10^{-3}$ Torr. More generally, the mean free path of neutral particles flying within the specimen chamber 24 without any collision is sufficiently longer than the total flying distance of a neutral particle.

Figure 3:
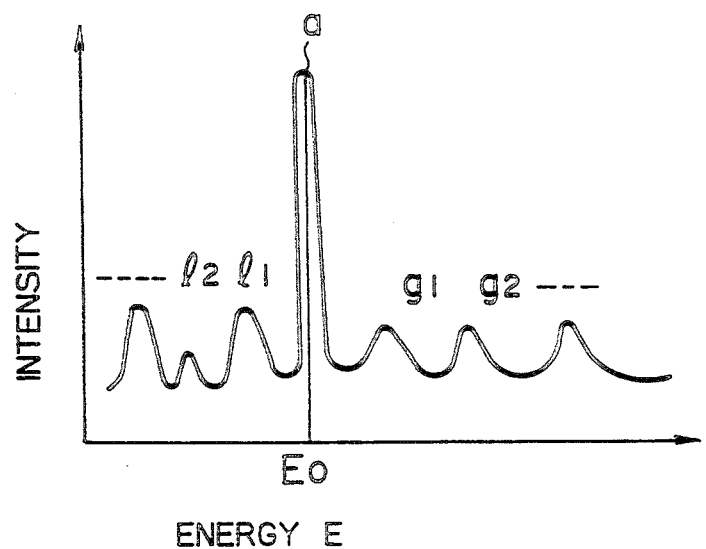
FIG. 3 is an example of a special distribution curve of the energy of reflected particles according to the present invention.

FIG. 3 shows an example of a measurement of the energy distribution of a neutral particle beam 5′ reflected or scattered from a specimen surface. The abscissa represents the energy of a neutral particle, and the ordinate represents the intensity (flux of particle flow) thereof. In FIG. 3, a large peak a at energy Eo corresponds to an incident neutral particle of a specimen which was subjected to elastic scattering (scattering without energy transfer). Peaks g1, g2, ... on the high energy side of the peak a correspond to those neutral particles which received energy from a specimen surface upon reflection or scattering therefrom, whereas peaks l1, l2, ... on the low energy side of the peak a correspond to those neutral particles which gave energy to the specimen surface. From the positions of peaks g1, g2, ... and l1, l2, ... and the amplitudes thereof, it is possible to know the type, quantity, and chemical bonding state of atoms present on the specimen surface.

In order to obtain spectra of high resolution, the width of each peak g1, g2, ..., l1, l2, ... should be made narrow. It is accordingly necessary to make narrow the energy width (i.e., width of peak a) of the incident neutral particle beam. This is because the energy width of an incident neutral particle beam reflects upon the energy width of a reflected or scattered neutral particle beam.

In order to make narrow the energy width of peak a, it is necessary either to raise the gas pressure within the vessel 2 for enhancement of the adiabatic cooling effect when gas is blown out, or to lower the temperature of the gas within the vessel 2. If the gas pressure within the vessel 2 is made high, the gas flow inevitably becomes large, resulting in a need of an enormous exhausting system. From a practical view, it is therefore more effective to lower the temperature of the gas within the vessel.

The amount of an energy difference between peaks (e.g., between peaks g1 and g2) is in the order of the molecule vibration energy which is about $1 \times 10^{-3}$ to $10^{-1}$ eV. In order to separate peaks, the energy width of each peak (i.e., the energy width of an incident neutral particle beam) should be equal to or smaller than the above-mentioned inter-peak energy difference (b $1 \times 10^{-3}$ to $10^{-1}$ eV). This condition corresponds to the temperature of an incident neutral particle beam equal to or lower than 12° to 1200° K. In order to realize this condition, the temperature of the gas within the vessel 2 is preferably equal to or lower than the liquid nitrogen temperature 77.4° K. (about 80° K.) when considering the adiabatic cooling effect at the time of gas blowing-out, and also considering the cooling method suitable for practical use. In such a case, liquid nitrogen is used as the coolant for the cooling means 3. In order to further improve the resolution, it is necessary to cool the temperature of the gas within the vessel 2 to about 20° K. or 10° K. by using liquified He gas as the coolant.

Figure 4:
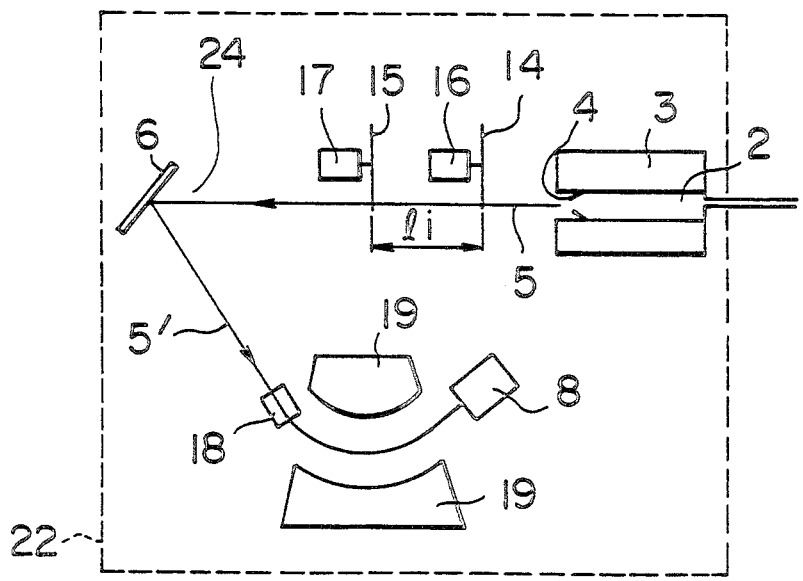
FIGS. 4 and 5 are schematic diagram showing other embodiments of this invention.
Figure 2:
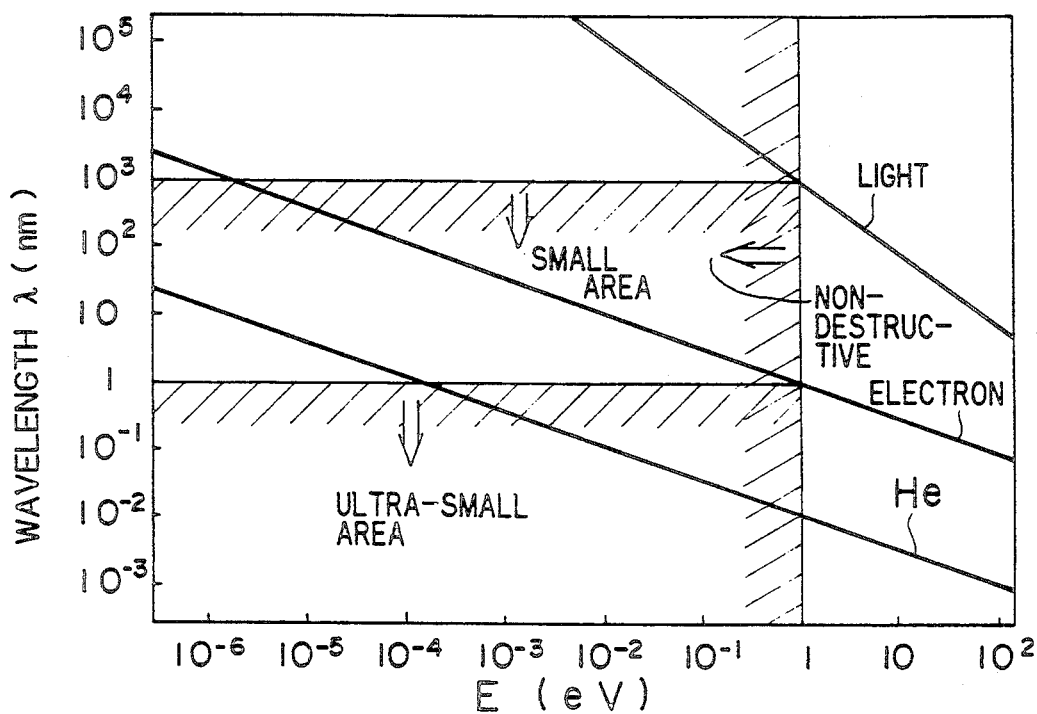
FIG. 2 is a graph showing the relationship between the energy and wavelength of light wave, electron wave, and He atom wave.

FIG. 4 shows another embodiment of this invention. In this embodiment, choppers 14 and 15 at two successive stages are used for obtaining an incident neutral particle beam 5 having a narrow energy width. The choppers 14 and 15 are spaced by a distance li and driven (rotated) by chopper driving motors 16 and 17. A particle beam is allowed to pass both the choppers 14 and 15 only when the chopper 15 is held open at the time a neutral particle has passed the chopper 14 and flown over the distance li and reach the chopper 15. Namely, only those neutral particles having a certain speed (and hence, a certain energy) are selected. With this arrangement, it is possible to obtain an incident neutral particle beam 5 having a narrow energy width.

In FIG. 4, there is also illustrated another method of analyzing the energy of a neutral particle beam 5' reflected or scattered from a specimen surface. First, the neutral particle beam 5' is ionized by ionizing means 18. Energies of generated ions are separated by an electrostatic type energy analyzer and detected by a detector 8. The kinetic energy of an ionized particle should be equal to the original energy of the neutral particle. As ionizing means, a method using a low speed electron beam or light beam is effective. According to a method using an electrostatic type energy analyzer, while a voltage is applied across opposing electrodes, the locus of an ion beam is changed by electrostatic force to thereby analyze the energy. With this embodiment method, energy analysis can be performed more precisely than the flying time method described with FIG. 1.

Figure 5:
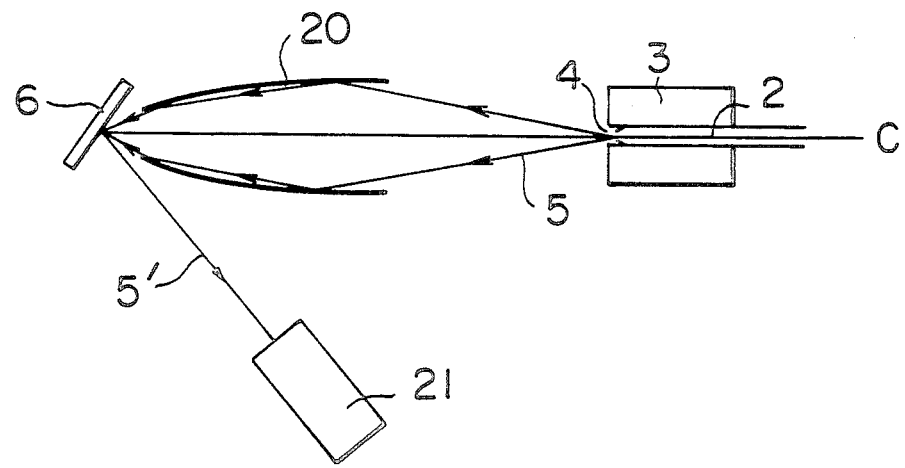

FIG. 5 shows a still further embodiment of this invention. In this embodiment, a neutral particle beam is converged by a lens 20 to allow surface measurement of a small area. Transfer of energy or momentum of a neutral particle at a specimen surface is measured with an energy analyzer 21. The lens 20 is made of a tubular body which is rotationally symmetric to a central axis C. A neutral particle beam 5 is mirror-reflected at the inner surface of the lens and thereby converged. The reflected angle of a particle beam incident to a lens local area point is the same as the incident angle, with respect to the normal axis at that point. A specimen 6 is set at a position where the neutral particle beam is converged by the lens 20. The specimen is one- or two-dimensionally driven relative to the particle beam. The energy of a reflected or scattered particle beam at the specimen surface is analyzed by the energy analyzer 21, to thereby check a linear or area energy distribution on the specimen surface. The specimen should be driven at a precision of 1 to 100 nm, so it is preferable to use a piezo actuator. The diameter (convergence diameter) of a neutral particle beam at the specimen surface may be changed as desired. It is particularly useful to set it equal to or smaller than 1 $\mu$m for the evaluation of semiconductor devices o material evaluation.

If He gas is used as a source of neutral particles, most of the particles incident to the lens are reflected because He is chemically inactive. In order to ensure mirror reflection, the de Broglie wavelength of an incident particle should be equal to or longer than the distance between atoms constituting the material of the lens reflection surface. The distance between ordinary atoms is in the order of 0.1 nm, whereas the de Broglie wavelength of a He particle is equal to or longer than 0.1 nm if the energy is equal to or smaller than about $10^{-3}$ eV. To realize such an arrangement, the temperature of the vessel 2 is required to be set equal to or lower than 20° K.

It is also desirable not to change the energy of a neutral particle when it is reflected at the lens 20. To this end, the weight (atomic number) of an atom of the material constituting the lens reflection surface is preferably sufficiently larger than that of a He atom. The material of the reflection surface is preferably chemically stable in order to always maintain it clean. Materials satisfying these conditions are Au, Pt, Ag, and Cu. It is preferable accordingly to make a lens by using one of these materials or to coat the reflection surface with one of these materials. However, this is not always required.

The lens 20 used in this embodiment has a rotation symmetry relative to the central axis C. The embodiment is not limited thereto, but an ordinary curved surface may also be used to converge a particle beam. The lens may be cooled or heated by temperature control means if necessary. Heating (flashing) is effective for maintaining clean the lens reflection surface, and cooling is effective for preventing energy change of a neutral particle when it is reflected at the lens (during its inherent operation).

In the above embodiment, convergence of a neutral particle beam is performed by using the phenomenon that it reflects at the solid surface of a lens. Obviously, other methods of converging a particle beam may also be used. For example, the locus of a neutral particle may be converged by a laser, gravitational force, or a strong electromagnetic field.

In the above embodiment, the advantageous features obtained by converging a neutral particle beam have been described. The locus of a neutral particle beam may obviously be changed even if it is not converged.

Surface measurement according to this invention may be carried out in cosmic space without using air exhausting equipment.

The lens 20 will be described in more detail. As shown in FIG. 5, a neutral particle beam 5 is arranged to reflect two times at the lens 20, in order to make small the aberration of the lens. As lenses of a twofold reflection type, there are Wolter optical systems, Kirkpatrik Beaz optical systems, Schwartzschild optical systems and the like. Tandem type optical systems may also be used. If a neutral particle beam is not required to be converged into a small spot (aberration gives rise to no problem), twofold reflection is not always required, and one reflection is sufficient. In the latter case, in place of the above-mentioned optical systems, various types of reflecting mirrors may be used, such as spherical reflecting mirrors, quadratic surface reflecting mirrors, and the like.

Further, considering a neutral particle beam as a wave from the standpoint of quantum mechanics as described previously, it becomes possible to converge a neutral particle beam by using diffraction effects such as a zone plate. This method is particularly useful for a neutral particle beam having a de Broglie wavelength equal to or longer than 1 Å. A zone plate is used in place of the lens 20 shown in FIG. 5.

We claim:

1. A surface measuring method, comprising the steps of:
   (a) blowing out neutral particles;
   (b) forming said blown-out particles into a beam;
   (c) controlling a locus of said neutral particle beam, including converging said neutral particle beam by directing said neutral particle beam at a solid body surface such that said surface reflects a beam having a controlled locus;
   (d) colliding said controlled locus neutral particle beam against a surface of a specimen such that neutral particles are reflected off of specimen surface;
   (e) detecting said neutral particles reflected from said specimen surface; and
   (f) analyzing the energy of said detected neutral particles.

2. A method according to claim 1, wherein said neutral particle blowing-out step includes a step of controlling the total energy of said neutral particles to have a value equal to or lower than 1 eV.

3. A method according to claim 1, further comprising a step of obtaining the total energy of said blown-out neutral particles as the sum of translational, vibrational and rotational energies of said blown-out particles.

4. A method according to claim 1, wherein said neutral particle is a rare gas atom.

5. A method according to claim 1, wherein said neutral particle is a He atom.

6. A method according to claim 1, wherein the surface of said solid body is coated with a material of at least one of, a mixture of two of, or a material partially consisting of at least one of Au, Pt, Ag. and Cu.

7. A method according to claim 1, wherein said analyzing step includes a step of measuring a transfer of energy or kinetic momentum of said neutral particle beam at said specimen surface by means of a flying time method.

8. A method according to claim 1, wherein said analyzing step includes a step of measuring a transfer of energy or kinetic momentum of said neural particle beam at said specimen surface by means of an electrostatic type energy analyzer.

9. A surface measuring method, comprising the steps of:
   (a) evacuating a space;
   (b) cooling gas containing neutral particles;
   (c) blowing out said cooled gas containing said neutral particles into said evacuated space;
   (d) forming said blown-out neutral particles into a neutral particle beam;
   (e) controlling a locus of said neutral particle beam, including converging said neutral particle beam by one of reflecting said neutral particle beam off of a solid body surface, and by using a lens that changes said locus with diffraction effects;
   (f) colliding said controlled locus neutral particle beam against a surface of a specimen such that neutral particles are reflected off of said specimen surface;
   (g) detecting said neutral particles reflected off of said specimen surface; and
   (h) analyzing the energy of said detected neutral particles.

10. A method according to claim 9, wherein said cooling step includes a step of cooling said gas equal to or lower than 80° K.

11. A method according to claim 9, wherein said evacuating step includes a step of differentially pumping a space for forming said neutral particle beam and a space for mounting said specimen.

12. A method according to claim 9, wherein the surface of said solid body is coated with a material of at least one of, a mixture of two of, or a material partially consisting of at least one of, Au, Pt, Ag and Cu.

13. A method according to claim 9, wherein said neutral particle is a rare gas atom.

14. A method according to claim 9, wherein said neutral particle is a He atom.

15. A method according to claim 9, wherein said analyzing step includes a step of measuring a transfer of energy or kinetic momentum of said neutral particle beam at said specimen surface by means of a flying time method.

16. A method according to claim 9, wherein said analyzing step includes a step of measuring a transfer of energy or kinetic momentum of said neutral particle beam at said specimen surface by means of an electrostatic type energy analyzer.

17. A surface measuring apparatus, comprising:
   (a) means for blowing out neutral particles;
   (b) means for forming said blown-out particles into a beam;

(c) means for controlling a locus of said neutral particle beam by one of reflecting said neutral particle beam off of a solid body surface, and using a lens that changes said locus with diffraction effects, including means for converging said neutral particle beam;

(d) means for colliding said controlled locus neutral particle beam against a surface of a specimen such that neutral particles are reflected off of said specimen surface;

(e) means for detecting said neutral particles reflected from said specimen surface; and (f) means for analyzing the energy of said detected neutral particles.

18. An apparatus according to claim 17, wherein said neutral particle blowing-out means includes means for controlling the total energy of said neutral particles to have a value equal to or lower than 1 eV.

19. An apparatus according to claim 17, wherein said neutral particle is a rare gas atom.

20. An apparatus according to claim 17, wherein said neutral particle is a He atom.

21. An apparatus according to claim 17, wherein the surface of said solid body is coated with a material of at least one of, a mixture of two of, or a material partially consisting of at least one of, Au, Pt, Ag and Cu.

22. An apparatus according to claim 17, wherein said analyzing means includes means for measuring a transfer of energy or kinetic momentum of said neutral particle beam at said specimen surface by means of a flying time method.

23. An apparatus according to claim 17, wherein said analyzing means includes means for measuring a transfer of energy or kinetic momentum of said neutral particle beam at said specimen surface by means of an electrostatic type energy analyzer.

24. An apparatus according to claim 17, wherein said blowing-out means includes means for cooling said gas containing said neutral particle.

25. An apparatus according to claim 24, wherein said cooling means includes means for cooling said gas equal to or lower than 80° K.

26. An apparatus according to claim 17, further comprising means for evacuating a space within which said neutral particle flies.

27. A surface measuring apparatus according to claim 17, wherein said reflective solid body surface is an inner surface of a lens.

28. A surface measuring apparatus according to claim 27, wherein said lens has a tubular body which is rotationally symmetric to a central axis.

29. A surface measuring apparatus according to claim 28, wherein said inner surface is coated with at least one of Au, Pt, Ag, and Cu.

30. A surface measuring method, comprising the steps of:

(a) blowing out neutral particles;

(b) forming said blown-out particles into a beam;

(c) controlling a locus of said neutral particle beam by using a reflective surface for changing said locus using diffraction effects to focus said neutral particle beam;

(d) colliding said controlled neutral particle beam against a surface of a specimen such that neutral particles are reflected off of said specimen surface;

(e) detecting said neutral particles reflected from said specimen surface; and analyzing the energy of said detected neutral particles.

* * * * *